United States Patent [19]
Boissonneault

[11] Patent Number: 4,962,098
[45] Date of Patent: Oct. 9, 1990

[54] GRADUATED ESTROGEN CONTRACEPTIVE

[75] Inventor: Roger M. Boissonneault, Long Valley, N.J.

[73] Assignee: Warner-Lambert Company, Morris Plains, N.J.

[21] Appl. No.: 340,974

[22] Filed: Apr. 20, 1989

Related U.S. Application Data

[63] Continuation-in-part of Ser. No. 61,646, Jun. 15, 1987, abandoned, which is a continuation-in-part of Ser. No. 659,144, Oct. 9, 1984, abandoned.

[51] Int. Cl.⁵ .............................................. A61K 31/56
[52] U.S. Cl. ..................................... 514/170; 514/843
[58] Field of Search ........................................ 514/170

[56] References Cited

U.S. PATENT DOCUMENTS

| | | | |
|---|---|---|---|
| 4,378,356 | 3/1983 | De Jager | 514/70 |
| 4,390,531 | 6/1983 | Edgren | 514/170 |
| 4,425,339 | 1/1984 | Pitchford | 514/170 |
| 4,544,554 | 10/1985 | Pasquale | 514/170 |

*Primary Examiner*—Joseph A. Lipovsky
*Attorney, Agent, or Firm*—Ronald A. Daignault

[57] ABSTRACT

Contraceptive methods and delivery systems involving few undesirable side effects during administration are based on novel triphasic estrogen/progestogen combinations, wherein the amount of estrogen is increased stepwise over the three phases.

9 Claims, No Drawings

GRADUATED ESTROGEN CONTRACEPTIVE

This is a continuation-in-part of U.S. application Ser. No. 61,646 filed June 15, 1987 which, in turn, is a continuation-in-part of application Ser. No. 659,144 filed Oct. 9, 1984, both abandoned.

BACKGROUND

The study of the prevention of pregnancy in human females has led to the evolution of many hormone-based compositions. Some compositions contain both estrogenic and progestogenic compounds. Such compositions, referred to herein as "estrogen/progestogen combinations", are highly effective in controlling ovulation and conception.

It has long been recognized that the progestin component is primarily responsible for the efficacy of the combination oral contraceptive. When original researchers attempted to synthesize pure progesterone, estrogen was a common contaminant. It was at this point that researchers realized that small quantities of estrogen could significantly minimize the major unwanted side effect, breakthrough bleeding or spotting. Small amounts of estrogen helped stabilize the endometrium and allowed cyclic withdrawal bleeding, similar to the natural menstral cycle. Initially, the doses of estrogen in combination oral contraceptives were quite high (150 mcg). To minimize estrogen's major negative side effect on blood clotting (30-35 mcg). However, as estrogen doses decreased, the incidences of unwanted breakthrough bleeding or spotting have generally increased. Most recently a new family of oral contraceptives (multiphasics) have been introduced that mimic the natural rise of progesterone over the cycle in an attempt to solve this problem. The present invention relates to the discovery that the side effects of breakthrough bleeding or spotting can be minimized by (1) a gradual increase of the estrogenic component throughout the cycle, (2) an increase of the ratio of estrogen/progestin throughout the cycle, (3) administration of those combinations at appropriately-timed intervals.

THE INVENTION

It has been discovered that the unwanted side effects generally associated with the administration of estrogen/progesterone contraceptive schemes can be minimized when the compositions used correspond to phases containing, in sequence, about 0.15-1.5 mg norethindrone acetate and about 10-50 mcg ethinyl estradiol for the first phase (Phase I); about 0.5-1.5 mg norethindrone acetate and about 10-50 mcg ethinyl estradiol in the second phase (Phase II); about 0.5-1.5 mg norethindrone acetate and about 10-50 mcg ethinyl estradiol in the third phase (Phase III) and a suitable quantity of an iron supplement, e.g., ferrous fumarate, or other non-steroidal agent or placebo in an optional fourth, or inactive, phase (Phase IV). It is essential that the phases succeed each other in increasing order (i.e., I, II, III, IV).

Applicant's combinations can be characterized in that the amount of estrogen is increased with each succeeding phase. That is, the amount of ethinyl estradiol or other estrogenic component is increased for each composition with different compositions being used in each phase.

U.S. Pat. No. 4,390,531 uses norethindrone as the progestogenic component in one type of estrogen/progestogen combination. However, such combinations are generally associated with high incidence of breakthrough bleeding. U.S. Pat. No. 390,531 describes a product(s) which attempts to mimic the phases of the natural menstrual cycle by varying the progestational component. Applicant uses stepwise increases in estrogen (graduated estrogen) rather than attempting to mimic natural physiology. Furthermore, Applicant utilizes norethindrone acetate which is structurally different from norethindrone and is associated with a more potent antiestrogenic effect upon the endometrium.

Applicant's four-phase system can be administered in 23- to 34-day cycles, with 21- to 28-day cycles preferred. Generally, the first phase will be about 4 to 7 days; the second will be about 5 to 8 days; the third will be about 7 to 12 days; and the fourth, or last, will be about 7 days.

ADVANTAGES

The invention has several advantages over prior art methods which employ estrogen/progestogen combinations. Principal among its advantages are ease of administration and the benefits of graduated estrogen, i.e., low amounts of estrogen are used early in the cycle when the endometrium is underdeveloped and increasing amounts of estrogen later in the cycle to add stability to the developing and mature endometrium.

In addition, use of the invention will potentially produce fewer side effects, most particularly, breakthrough bleeding and nausea. The compositions used herein preferably contain norethindrone acetate, a progestogenic component having less potency—and, comcomitantly, producing lower incidence of breakthrough bleeding—than other progestogenic agents, e.g., norethindrone.

Other advantages and aspects of the invention will be apparent from a consideration of the following description.

DESCRIPTION OF THE INVENTION

The invention covers a method and kit for the use of a graduated multiphase, sequentially-administered combination of compositions.

In one aspect, the invention deals with a method of contraception comprising the steps of sequentially administering, to a female of child bearing age:

(1) for about 4 to about 7 days, a composition I containing norethindrone acetate and ethinyl estradiol, (2) for about 5 to about 8 days, a composition II containing norethindrone acetate and ethinyl estradiol, (3) for about 7 to 12 days, a composition III containing norethindrone acetate and ethinyl estradiol, wherein the amount of estrogen is increased stepwise over the three compositions, and (4) for about 7 days, a composition IV containing ferrous fumarate.

In another aspect, the invention is concerned with a graduated multiphase combination and contraceptive kit comprising a package containing daily dosages of:

(1) a Phase I composition containing norethindrone acetate and ethinyl estradiol;

(2) a Phase II composition containing norethindrone acetate and ethinyl estradiol; and (3) a Phase III composition containing norethindrone acetate and ethinyl estradiol, wherein the amount of estrogen is increased stepwise over the three compositions.

An optional Phase IV composition, which contains an iron supplement, e.g., ferrous fumarate, and/or one or more placebos, can be used in conjunction with the other three.

The compositions are consumed or administered in a numeric sequence with the Phase I composition being used first, the Phase II composition being used second, etc. If packaging and/or other requirements dictate, the method and kit described herein can be employed as part of a larger scheme for contraception or treatment of gynecological disorders. While the sequence in which Applicant's combinations are administered is important to their operation, it should be kept in mind that variations in timing and dosage can be tolerated when medical considerations so dictate.

The compositions employed in accordance with the invention will preferably contain in Phase I. about 0.5-1.5 mg norethindrone acetate and about 10-30 mcg ethinyl estradiol, in Phase II about 0.5-1.5 mg norethindrone acetate and about 20-40 mcg ethinyl estradiol, and in Phase III about 0.5-1.5 mg norethindrone acetate and about 30-50 mcg ethinyl estradiol, wherein the amount of ethinyl estradiol is increased stepwise over the three compositions.

The compositions employed in accordance with the invention in Phases I through IV will more preferably have the administration times and drug contents set forth in the following tables when a four-phase system is used. Each table sets forth relevant values for one of Applicant's preferred embodiments, or configurations, for administration of the system to females.

TABLE 1

| | (Configuration A) | | | |
|---|---|---|---|---|
| Phase | Administration Interval, Days | Norethindrone Acetate, mg | Ethinyl Estradiol, mcg | Ferrous Fumarate, mg |
| I | 5 | 1.0 | 20 | 0 |
| II | 7 | 1.0 | 30 | 0 |
| III | 9 | 1.0 | 35 | 0 |
| IV | 7 | 0 | 0 | 75 |

TABLE 2

| | (Configuration B) | | | |
|---|---|---|---|---|
| Phase | Administration Interval, Days | Norethindrone Acetate, mg | Ethinyl Estradiol, mcg | Ferrous Fumarate, mg |
| I | 5 | 1.0 | 20 | 0 |
| II | 7 | 1.5 | 30 | 0 |
| III | 9 | 1.0 | 50 | 0 |
| IV | 7 | 0 | 0 | 75 |

TABLE 3

| | (Configuration C) | | | |
|---|---|---|---|---|
| Phase | Administration Interval, Days | Norethindrone Acetate, mg | Ethinyl Estradiol, mcg | Ferrous Fumarate, mg |
| I | 5 | 1.0 | 20 | 0 |
| II | 7 | 1.0 | 30 | 0 |
| III | 9 | 1.0 | 40 | 0 |
| IV | 7 | 0 | 0 | 75 |

The norethindrone acetate used in the tables is Norlutate®, a product manufactured by the Parke-Davis Division of the Warner-Lambert company, Morris Plains, N.J.

The designation "mcg" refers to micrograms and "mg" to milligrams.

It should be noted that these tables are presented for illustrative purposes only. The substitution of functionally equivalent amounts and kinds of reagent(s) in these schemes is contemplated. For example, the use of su9ar or other placebo in place of all or part of the ferrous fumarate is envisioned.

In addition, the use of other conventional additives, e.g., fillers, colorants, polymeric binders, and the like is also contemplated. In general any pharmaceutically-acceptable additive which does not interfere with the function of the active components can be used in one or more of the compositions.

Suitable carriers with which the compositions can be administered include lactose, starch, cellulose derivatives and the like used in suitable amounts. Lactose is a preferred carrier. Mixtures of carriers are operable.

While the norethindrone acetate component is a strict requirement, the ethinyl estradiol component can be completely or partially replaced with one or more conventional estrogenic substances, e.g., mestranol.

While the invention is discussed as one employing four phases, it may employ only three. Phase IV is not essential to the operation of the other three distinct phases. Thus a method or kit which does not contain the Phase IV component is operable and, in fact, will be preferred when suitable factors, e.g., economy, dictate the non-use of the Phase IV component.

The terms "method" and "kit" are used herein to encompass any drug delivery systems via the use of which the 3- or 4-phase scheme outlined above can be effectively administered to human females. Combinations of various dosage forms are operable.

A unique dosage pattern, i.e., a unique sequence of administrations of a novel estrogen/progestogen combination has been discovered which minimizes certain side effects, notably breakthrough bleeding, commonly associated with conventional low dosage pills.

Reasonable variations, such as those which would occur to a skilled artisan, can be made herein without departing from the scope of the invention.

I claim:

1. A method of contraception comprising the steps of sequentially-administering to a female of child bearing age:
    (1) for about 4 to about 7 days, a composition I containing about 0.5-1.5 mg norethindrone acetate and about 10-50 mcg ethinyl estradiol,
    (2) for about 5 to about 8 days, a composition II containing about 0.5-1.5 mg norethindrone acetate and about 10-50 mcg ethinyl estradiol, and
    (3) for about 7 to about 12 days, a composition III containing 0.5-1.5 mg norethindrone acetate and about 10-50 mcg ethinyl estradiol, wherein the amount of ethinyl estradiol is increased stepwise by the amount of at least 5 mcg in each step.

2. The method of claim 1 which comprises the additional step of administering, for about 7 days, a composition IV containing ferrous fumarate.

3. The method of claim 1 wherein composition I contains about 0.5-1.5 mg norethindrone acetate and about 10-30 mcg ethinyl estradiol; composition II contains 0.5-1.5 mg norethindrone acetate and 20-40 mcg ethinyl estradiol; and composition III contains 0.5-1.5 mg norethindrone acetate and about 30-50 mcg ethinyl estradiol.

4. The method of claim 1 wherein composition I is administered for about 5 days and contains about 1.0 mg norethindrone acetate and about 20 mcg ethinyl estradiol; composition II is administered for about 7 days and contains about 1.0 mg norethindrone acetate and about 30 mcg ethinyl estradiol; and composition III is administered for about 9 days and contains about 1.0 mg norethindrone acetate and about 40 mcg ethinyl estradiol.

5. The method of claim 4 wherein the compositions are administered in combination with a suitable carrier.

6. The method of claim 1 wherein composition I is administered for about 5 days and contains about 1.0 mg norethindrone acetate and about 20 mcg ethinyl estradiol; composition II is administered for about 7 days and contains about 1.5 mg norethindrone acetate and about 30 mcg ethinyl estradiol; and composition III is administered for about 9 days and contains about 1.0 mg norethindrone acetate and about 50 mcg ethinyl estradiol.

7. The method of claim 6 wherein the compositions are administered in combination with a suitable carrier.

8. The method of claim 1 wherein composition I is administered for about 5 days and contains about 1.0 mg norethindrone acetate and about 20 mcg ethinyl estradiol; composition II is administered for about 7 days and contains about 1.0 mg norethindrone acetate and about 30 mcg ethinyl estradiol; and composition III is administered for about 9 days and contains about 1.0 mg norethindrone acetate and about 35 mcg ethinyl estradiol.

9. The method of claim 8 wherein the compositions are administered in combination with a suitable carrier.

* * * * *